(12) United States Patent
Allen, IV

(10) Patent No.: US 11,553,938 B2
(45) Date of Patent: *Jan. 17, 2023

(54) SURGICAL INSTRUMENTS, CONTROL ASSEMBLIES, AND SURGICAL SYSTEMS FACILITATING MANIPULATION AND VISUALIZATION

(71) Applicant: COVIDIEN LP, Mansfield, MA (US)

(72) Inventor: James D. Allen, IV, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 935 days.

This patent is subject to a terminal disclaimer.

(21) Appl. No.: 16/385,063

(22) Filed: Apr. 16, 2019

(65) Prior Publication Data

US 2019/0336155 A1  Nov. 7, 2019

Related U.S. Application Data

(60) Provisional application No. 62/666,218, filed on May 3, 2018.

(51) Int. Cl.
*A61B 17/29* (2006.01)
*A61B 18/14* (2006.01)
(Continued)

(52) U.S. Cl.
CPC ...... *A61B 17/29* (2013.01); *A61B 17/320092* (2013.01); *A61B 18/1445* (2013.01);
(Continued)

(58) Field of Classification Search
CPC ............ A61B 17/29; A61B 17/320092; A61B 18/1445; A61B 2017/00017; A61B 2017/00075; A61B 2017/00314; A61B 2017/00427; A61B 2017/00398; A61B 2017/0734; A61B 2017/2902; A61B 2017/2903; A61B 2017/2908;
(Continued)

(56) References Cited

U.S. PATENT DOCUMENTS

| 4,503,842 A | 3/1985 | Takayama |
| 5,350,355 A | 9/1994 | Sklar |

(Continued)

*Primary Examiner* — Michael F Peffley
(74) *Attorney, Agent, or Firm* — Carter, DeLuca & Farrell LLP

(57) ABSTRACT

A surgical instrument includes a housing, a shaft extending from the housing, an end effector assembly extending from the shaft and configured to rotate and/or articulate relative to the housing, a motor disposed within the housing and operably coupled to the end effector assembly to rotate and/or articulate of the end effector assembly relative to the housing, and a sensing assembly configured to sense movement of the housing relative to a reference position and to drive the motor to rotate and/or articulate of the end effector assembly relative to the housing based upon the sensed movement. The sensing assembly is configured to operate in each of a standard mode, wherein movement of the housing effects rotation and/or articulation of the end effector assembly in a similar direction, and a reversed mode, wherein movement of the housing effects rotation and/or articulation of the end effector assembly in an opposite direction.

20 Claims, 7 Drawing Sheets

(51) Int. Cl.
*A61B 34/30* (2016.01)
*A61B 90/00* (2016.01)
*A61B 17/32* (2006.01)
*A61B 17/00* (2006.01)

(52) U.S. Cl.
CPC .............. *A61B 34/30* (2016.02); *A61B 90/37* (2016.02); *A61B 2017/00075* (2013.01); *A61B 2017/00398* (2013.01); *A61B 2017/00734* (2013.01); *A61B 2017/2902* (2013.01); *A61B 2017/2903* (2013.01); *A61B 2017/2908* (2013.01); *A61B 2017/2946* (2013.01); *A61B 2017/320071* (2017.08); *A61B 2017/320074* (2017.08); *A61B 2034/301* (2016.02)

(58) Field of Classification Search
CPC .... A61B 2017/2927; A61B 2017/2929; A61B 2017/2946; A61B 2017/320017; A61B 2017/320074; A61B 2018/00982; A61B 2034/2048
See application file for complete search history.

(56) References Cited

U.S. PATENT DOCUMENTS

| | | | |
|---|---|---|---|
| 6,872,178 B2 | 3/2005 | Weinberg | |
| 7,922,061 B2 | 4/2011 | Shelton, IV et al. | |
| 7,955,327 B2 | 6/2011 | Sartor et al. | |
| 8,419,717 B2 | 4/2013 | Diolaiti et al. | |
| 2012/0221145 A1* | 8/2012 | Ogawa | B25J 13/02 700/254 |
| 2013/0038707 A1* | 2/2013 | Cunningham | G06V 20/20 382/131 |
| 2013/0123783 A1* | 5/2013 | Marczyk | A61B 18/1445 606/1 |
| 2013/0324999 A1 | 12/2013 | Price et al. | |
| 2014/0246471 A1* | 9/2014 | Jaworek | A61B 90/98 227/175.1 |
| 2014/0303643 A1 | 10/2014 | Ha et al. | |
| 2016/0302840 A1* | 10/2016 | Scheib | A61B 17/320092 |
| 2017/0172594 A1* | 6/2017 | Allen, IV | A61B 17/295 |
| 2017/0172606 A1* | 6/2017 | Riestenberg | A61B 17/320068 |
| 2018/0133521 A1* | 5/2018 | Frushour | A61B 17/320092 |

* cited by examiner

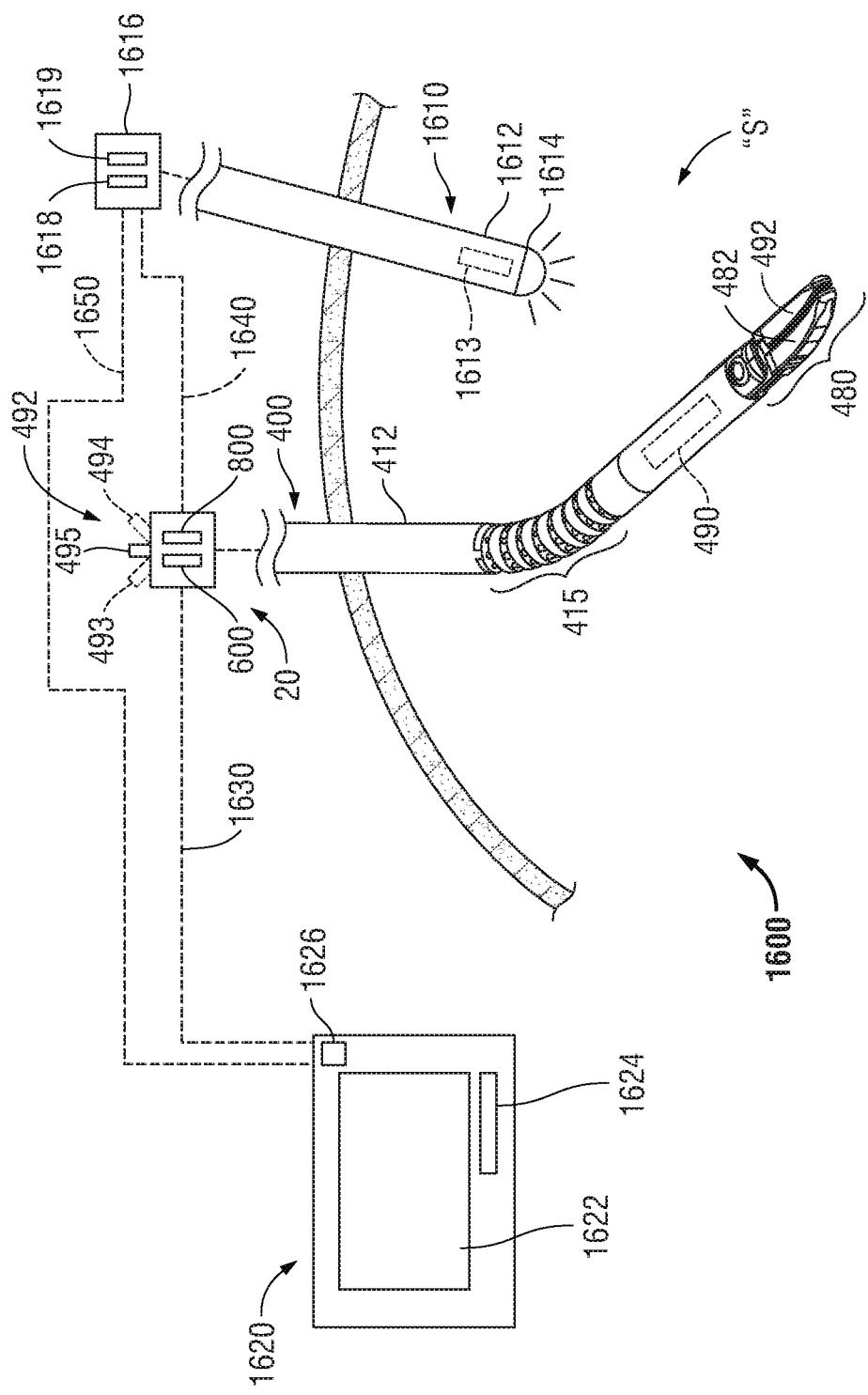

SURGICAL INSTRUMENTS, CONTROL ASSEMBLIES, AND SURGICAL SYSTEMS FACILITATING MANIPULATION AND VISUALIZATION

CROSS-REFERENCE TO RELATED APPLICATIONS

This application claims the benefit of and priority to U.S. Provisional Patent Application No. 62/666,218, filed on May 3, 2018, the entire contents of which are hereby incorporated herein by reference.

BACKGROUND

1. Technical Field

The present disclosure relates to surgical instruments and, more specifically, to surgical instruments including control assemblies and surgical systems incorporating the same that facilitate manipulation and visualization of a distal portion of the surgical instrument during use.

2. Discussion of Related Art

Endoscopic instruments have become widely used by surgeons in endoscopic surgical procedures because they enable surgery to be less invasive as compared to conventional open surgical procedures in which the surgeon is required to cut open large areas of body tissue. As a direct result thereof, endoscopic surgery minimizes trauma to the patient and reduces patient recovery time and hospital costs.

Some endoscopic instruments incorporate rotation and/or articulation features, thus enabling rotation and/or articulation of an end effector assembly of the endoscopic surgical instrument, disposed within the surgical site, relative to a handle assembly of the endoscopic surgical instrument, which remains externally disposed, to better position the end effector assembly for performing a surgical task within the surgical site. An endoscopic camera communicating with an operating room display is also often utilized in endoscopic surgery to enable the surgeon to visualize the surgical site as the end effector assembly is maneuvered into position and operated to perform the desired surgical task.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein. The term "endoscopic" as utilized herein is intended to encompass laparoscopic, minimally-invasive, natural-orifice, and reduced access. Also, the term "instrument" as utilized herein is intended to encompass handheld devices, mounted or supported device, and robotic devices.

Provided in accordance with aspects of the present disclosure is a surgical instrument including a housing, a shaft extending distally from the housing, an end effector assembly extending distally from the shaft and configured to rotate and/or articulate relative to the housing, a motor disposed within the housing and operably coupled to the end effector assembly to rotate and/or articulate the end effector assembly relative to the housing, and a sensing assembly configured to sense movement of the housing relative to a reference position and to drive the motor to rotate and/or articulate the end effector assembly relative to the housing based upon the sensed movement. The sensing assembly is configured to operate in each of a standard mode, wherein movement of the housing effects rotation and/or articulation of the end effector assembly in a similar direction, and a reversed mode, wherein movement of the housing effects rotation and/or articulation of the end effector assembly in an opposite direction.

In an aspect of the present disclosure, the end effector assembly is rotated and/or articulated at a speed proportional to displacement of the housing from the reference position (up to a maximum speed, in aspects).

In another aspect of the present disclosure, the motor is configured to rotate and articulate the end effector assembly.

In another aspect of the present disclosure, the motor is configured to rotate or articulate the end effector assembly and a second motor disposed within the housing is operably coupled to the end effector assembly. The second motor is configured to articulate the end effector assembly (in aspects where the other motor rotates the end effector assembly) or to rotate the end effector assembly (in aspects where the other motor articulates the end effector assembly).

In yet another aspect of the present disclosure, a rotation lockout is configured to prevent rotation of the end effector assembly in response to a sensed condition.

In still another aspect of the present disclosure, a manual selector associated with the housing is selectively movable to a first position or a second position to switch to the standard mode or the reversed mode, respectively.

In still yet another aspect of the present disclosure, the manual selector further includes a neutral position wherein the sensing assembly automatically switches between the standard mode and the reversed mode.

In another aspect of the present disclosure, the sensing assembly automatically switches between the standard mode and the reversed mode based upon a position of the end effector assembly. In aspects, the sensing assembly automatically switches between the standard mode and the reversed mode based upon a position of the end effector assembly relative to a surgical camera.

A surgical system provided in accordance with the present disclosure includes a surgical camera, a surgical display configured to display a video image received from the surgical camera, and a surgical instrument including a housing and an end effector assembly distally-spaced from the housing. The end effector assembly is configured to rotate and/or articulate relative to the housing. The surgical instrument further includes a sensing assembly configured to sense movement of the housing relative to a reference position and to effect rotation and/or articulation of the end effector assembly relative to the housing in response to the sensed movement. The sensing assembly is configured to operate in each of a standard mode, wherein movement of the housing effects rotation and/or articulation of the end effector assembly in a similar direction, and a reversed mode, wherein movement of the housing effects rotation and/or articulation of the end effector assembly in an opposite direction.

In an aspect of the present disclosure, the sensing assembly operates in the standard mode when reverse alignment visualization of the video image does not occur, and operates in the reversed mode when reverse alignment visualizing of the video image occurs.

In another aspect of the present disclosure, the sensing assembly automatically switches between the standard mode and the reversed mode based upon whether reverse alignment visualization occurs.

In still another aspect of the present disclosure, an indicator is provided to indicate to a user to switch to the standard mode or the reversed mode based upon whether reverse alignment visualization occurs.

In yet another aspect of the present disclosure, one or more position sensors operably associated with the end effector assembly and/or the surgical camera and configured to detect a position thereof. The occurrence of reverse alignment visualization is determined based upon the position of the end effector assembly or the surgical camera.

In still yet another aspect of the present disclosure, a first position sensor is operably associated with the end effector assembly and a second position sensor is associated with the surgical camera. In such aspects, the occurrence of reverse alignment visualization is determined based upon the relative positions of the end effector assembly and the surgical camera.

In another aspect of the present disclosure, the surgical instrument further includes a manual selector associated with the housing and selectively movable to a first position or a second position to switch to the standard mode or the reversed mode, respectively. In aspects, the manual selector further includes a neutral position wherein the sensing assembly automatically switches between the standard mode and the reversed mode based upon whether reverse alignment visualization occurs.

In still another aspect of the present disclosure, an indicator is provided to indicate occurrence of reverse alignment visualization to indicate to a user to move the manual selector to the second position.

In yet another aspect of the present disclosure, the surgical instrument further includes a rotation lockout configured to prevent rotation of the end effector assembly in response to a sensed condition.

BRIEF DESCRIPTION OF THE DRAWINGS

Various aspects and features of the present disclosure are described hereinbelow with reference to the drawings, wherein like numerals designate identical or corresponding elements in each of the several views and:

FIG. 6 is a schematic illustration of a surgical system provided in accordance with aspects of the present disclosure in use.

DETAILED DESCRIPTION

Figure 1:
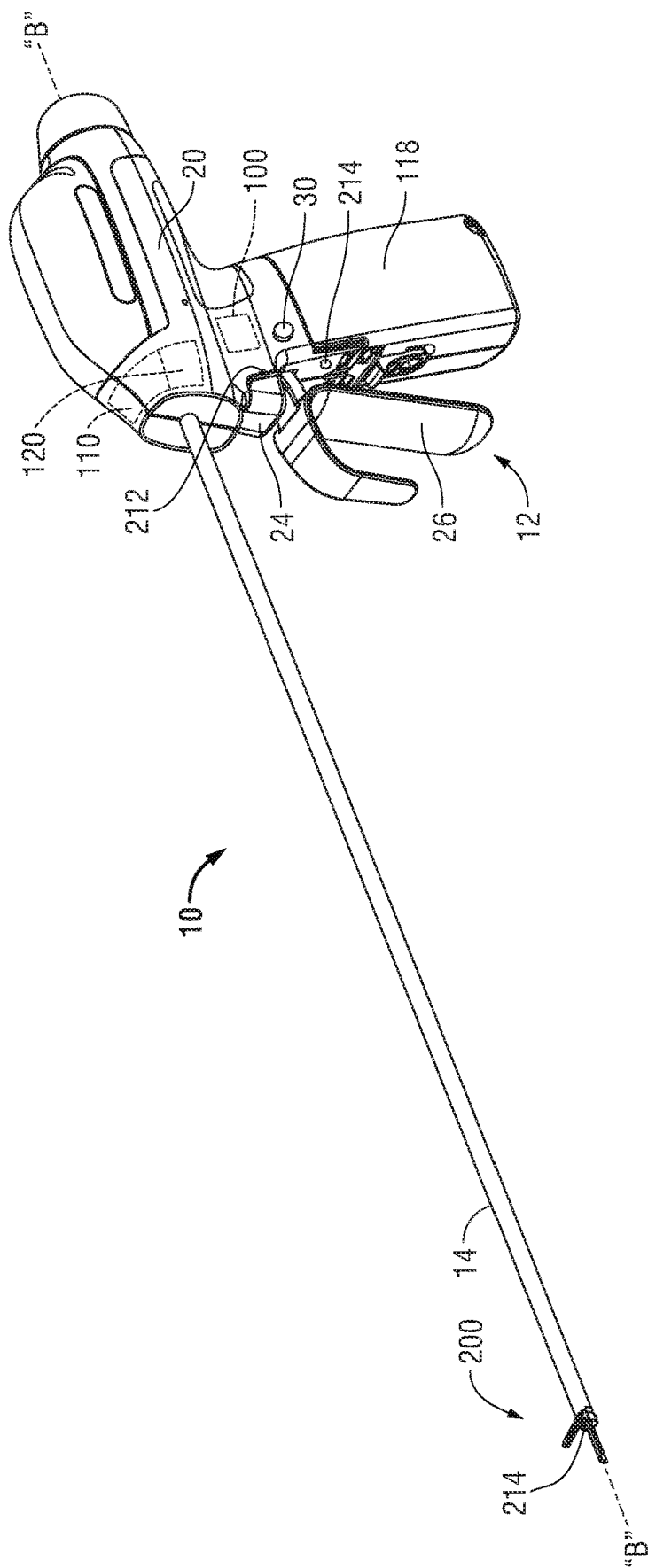
FIG. 1 is a perspective view of a surgical instrument provided in accordance with aspects of the present disclosure showing a motion sensor assembly in phantom.

Referring to FIG. 1, an endoscopic ultrasonic surgical instrument exemplifying aspects and features of the present disclosure is shown generally identified by reference numeral 10. Endoscopic ultrasonic surgical instrument 10 is configured to deliver ultrasonic energy to tissue; however, any other suitable endoscopic surgical instrument may be utilized in accordance with the aspects and features of the present disclosure such as, for example, an endoscopic surgical stapler, an endoscopic surgical clip applier instrument, an endoscopic surgical suturing instrument, an endoscopic electrosurgical surgical instrument, e.g., instrument 400 (FIGS. 4A-4B), the endoscopic portion of a robotic surgical system, e.g., robotic surgical system 1000 (FIG. 5), etc.

Instrument 10 generally includes a handle assembly 12, a shaft 14, a motion sensing assembly 100, and an end effector assembly 200 including a jaw member 210 movable relative to an ultrasonic blade 220 between an open position and a clamping position for clamping issue against ultrasonic blade 220.

Handle assembly 12 includes a housing 20 that supports a battery assembly 118 and a generator and transducer assembly 20, and includes an activation button 24 and a clamp trigger 26 operably coupled thereto. Shaft 14 defines a longitudinal axis "B-B" of instrument 10 and extends distally from handle assembly 12 to end effector assembly 200.

Battery assembly 118, upon activation of the activation button 24, is configured to supply power to the generator of generator and transducer assembly 20 to drive the ultrasonic transducer (not shown) of the generator and transducer assembly 20 which, in turn, is configured to produce ultrasonic energy for transmission along a waveguide (not shown) to ultrasonic blade 220 of end effector assembly 200 to treat, e.g., to coagulate, cauterize, fuse, cut, desiccate, fulgurate, or otherwise treat, tissue clamped between jaw member 210 and ultrasonic blade 220 or positioned adjacent to ultrasonic blade 220.

Battery assembly 118 and generator and transducer assembly 20 are each releasably secured to housing 20 of handle assembly 12, and are removable therefrom to facilitate disposal of handle assembly 12, with the exception of battery assembly 118 and generator and transducer assembly 20. However, any or all of the components of instrument 10 may be configured as disposable single-use components or sterilizable multi-use components, and/or that the surgical instrument 10 be connectable to a remote power source and/or generator rather than having such components onboard.

Continuing with reference to FIG. 1, clamp trigger 26 is operably associated with housing 20 of handle assembly 12 and is selectively manipulatable relative thereto to actuate a drive assembly (not shown) extending through handle assembly 12 and shaft 14 to move jaw member 210 relative to ultrasonic blade 220 between the open position and the clamping position.

Motion sensing assembly 100 includes a motor 110 configured to drive manipulation of end effector assembly 200 in response to movement of housing 20 of handle assembly 12. Handle assembly 12 can include a motion activation control 30 that activates motion sensing assembly 100. When motion activation control 30 is activated, motion sensing assembly 100 creates a home or reference position corresponding to the position of housing 20 of handle assembly 12 at that moment. This reference position is then stored in a memory of motion sensing assembly 100. Once the reference position is stored, motion sensing assembly 100 is able to detect movement of housing 20 of handle assembly 12 relative to the reference position and direct motor 110 to manipulate end effector assembly 200 in response to movement of housing 20 of handle assembly 12 relative to the reference position.

Motion sensing assembly 100 may include accelerometers, gyroscopes, and/or other suitable mechanisms configured to determine movement of housing 20 of handle assembly 12 relative to the reference position within a gravitational field. A microcontroller of motion sensing assembly 100 analyzes movement of housing 20 of handle assembly 12 within the gravitational field, based upon feedback from the accelerometers, gyroscopes, and/or other suitable mechanisms, and directs motor 110 to manipulate end effector assembly 200 in response to the movement of handle assembly 100. A storage device associated with the microcontroller of motion sensing assembly 100 stores one or more programs for execution by the microcontroller to perform the above.

Figure 2:
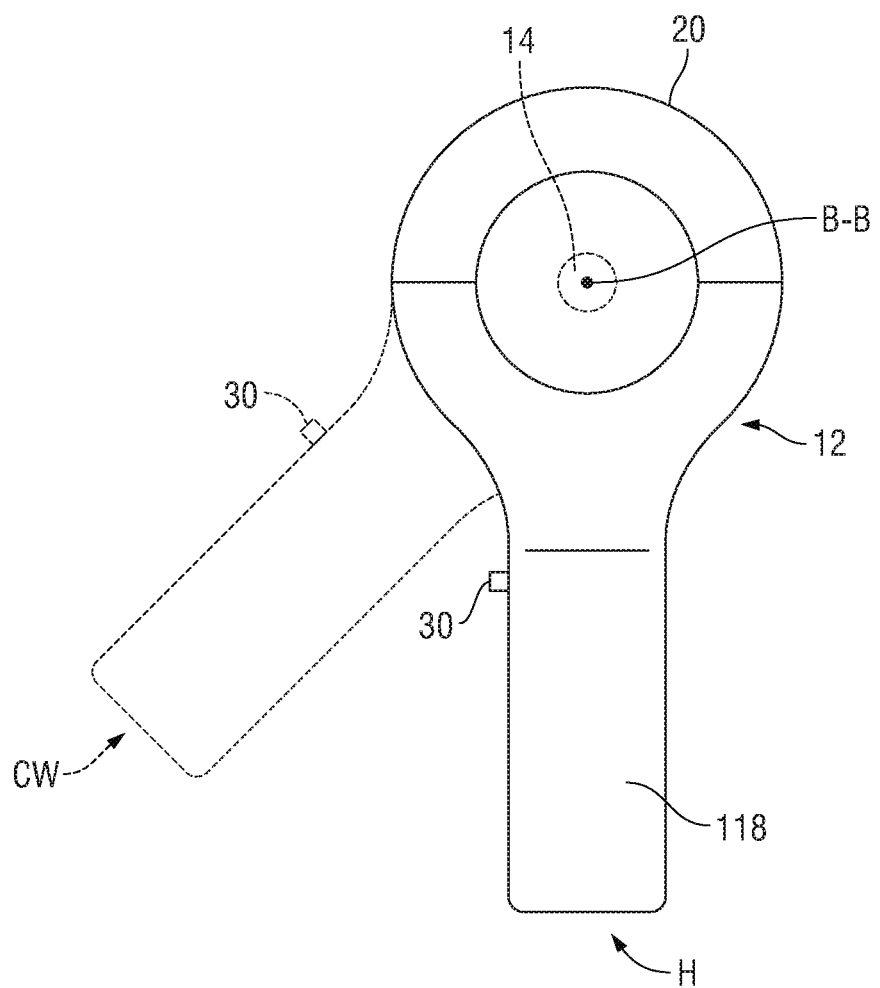
FIG. 2 is a rear view of the surgical instrument of FIG. 1.

With additional reference to FIG. 2, once motion activation control 30 has been activated to register home position "H" and thereafter housing 20 of handle assembly 12 is rotated from the home position "H" about the axis "B-B" in a clockwise direction, towards position "CW," for example, motor 110 rotates shaft 14 about the axis "B-B" and relative to housing 20 of handle assembly 12 which, in turn, rotates end effector assembly 200 at the distal end of shaft 14 relative to housing 20 of handle assembly 12 in a clockwise direction. As the radial displacement of housing 20 of handle assembly 12 about the axis "B-B" is increased, motor 110 increases the speed at which shaft 14 is rotated about the axis "B-B" relative to housing 20 of handle assembly 12. Similarly, as the radial displacement of handle assembly 12 about the axis "B-B" is decreased, motor 110 decreases the speed at which shaft 14 is rotated about the axis "B-B" relative to housing 20 of handle assembly 12. Position "CW" may represent a maximum angular speed of rotation of shaft 14 such that rotation beyond position "CW" ceases to increase the angular speed of rotation of shaft 14 relative to housing 20 of handle assembly 12. As shown, housing 20 of handle assembly 12 may reach the position "CW" after about it/4 or 45° of rotation; however, it is contemplated that position "CW" may be reached in a range of about it/6 or 30° to about it/2 or 90° of rotation. The maximum angular speed of rotation of shaft 14 may be in the range of about 5 rpm to about 30 rpm (e.g., about 15 rpm), although other speeds of rotation ranges are also contemplated. It will be appreciated that speed of rotation of shaft 14 is proportional to the rotation of housing 20 of handle assembly 12 about the axis "B-B" from the home position towards the position "CW."

Similarly, when housing 20 of handle assembly 12 is rotated from the home position H about the axis "B-B" in a counter-clockwise direction, motor 110 rotates shaft 14 about the axis "B-B," which rotates end effector assembly 200 relative to housing 20 of handle assembly 12 in a counter-clockwise direction.

Continuing to refer to FIGS. 1 and 2, instrument 10 may include a rotation lockout feature that can prevent rotation of end effector assembly 200 when certain conditions are met. For example, the rotation lockout feature can be configured to prevent rotation of end effector assembly 200 relative to housing 20 of handle assembly 12 while ultrasonic energy is delivered to end effector assembly 200. The rotation lockout feature may include a lockout switch 212 engagable by activation button 24 such that when activation button 24 is depressed to deliver ultrasonic energy, lockout switch 212 signals to the microcontroller of motion sensing assembly 100 to prevent rotation of end effector assembly 200 about the axis "B-B" relative to housing 20 of handle assembly 12.

Additionally or alternatively, the rotation lockout feature may prevent rotation of end effector assembly 200 relative to housing 20 of handle assembly 12 when jaw member 210 of end effector assembly 200 is in the clamping position. The rotation lockout feature, in such configurations, may include a lockout switch 214 disposed at end effector assembly 200 (or otherwise positioned) such that when jaw member 210 of end effector assembly 200 is in the clamping position, lockout switch 214 signals the microcontroller of motion sensing assembly 100 to prevent rotation of end effector assembly 200 about the axis "B-B" relative to housing 20 of handle assembly 12.

Instrument 10 may also include a torque limiting mechanism 120 that prevents excessive torque from being applied by motor 110 to rotate end effector assembly 200 about the axis "B-B" relative to housing 20 of handle assembly 12. Torque limiting mechanism 120 may be a mechanical coupler (e.g., a clutch) or an electronic limiter (e.g., a torque sensor in communication with motor 110). Torque limiting mechanism 120 may be positioned adjacent motor 110 or adjacent end effector assembly 200, or in any other suitable position.

Figure 3:
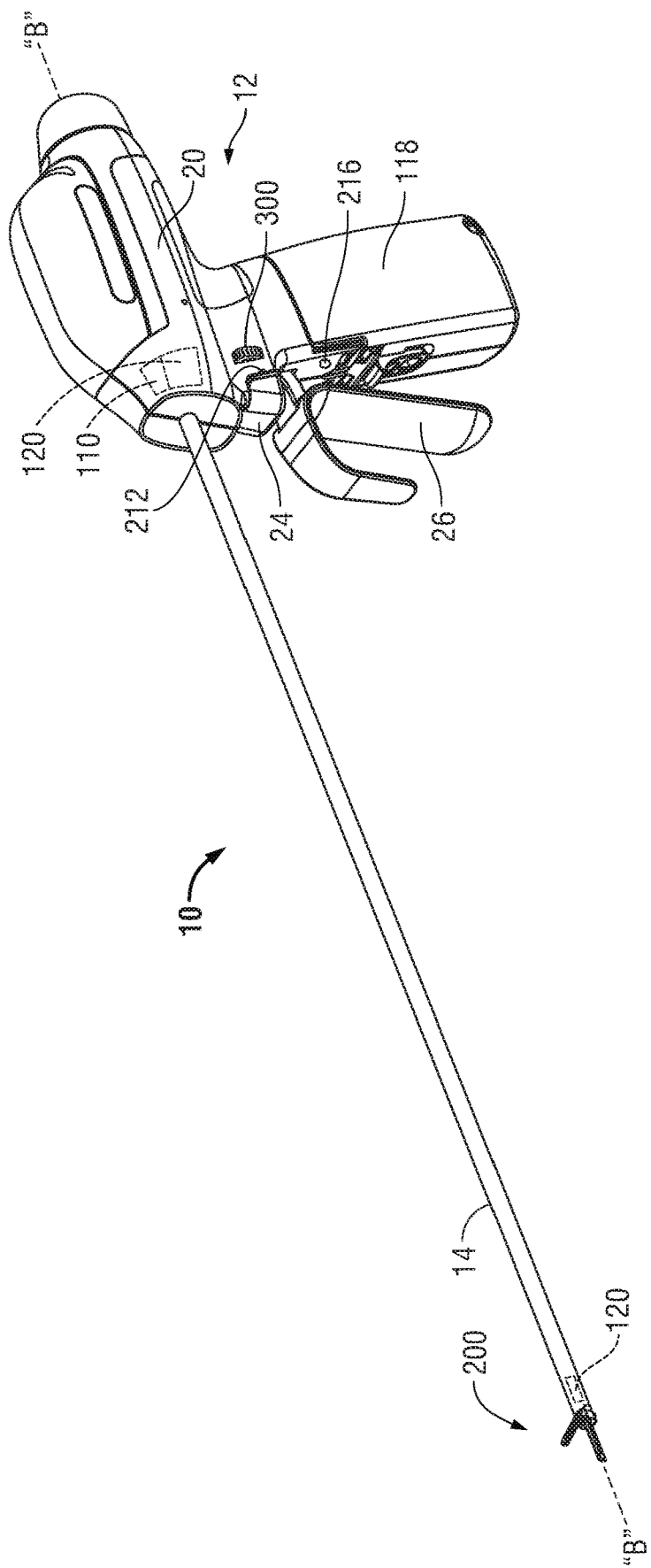
FIG. 3 is a perspective view of another configuration of the surgical instrument of FIG. 1.

Referring to FIG. 3, instrument 10, as an alternative to incorporating motion sensing assembly 100 (FIG. 1), may include a rotation control 300. Rotation control 300 is disposed on handle assembly 12 to control rotation of shaft 14 about the axis "B-B" relative to housing 20 of handle assembly 12 and, thus, rotation of end effector assembly 200 relative to housing 20 of handle assembly 12. Rotation control 300 can be in the form of a potentiometer that is engagable by the clinician such that rotation of rotation control 300 in a clockwise direction directs motor 110 to rotate shaft 14 about the axis "B-B" relative to housing 20 of handle assembly 12 in a clockwise direction. Rotation control 300 may be rotatable about a control axis that is parallel to the axis "B-B," or otherwise oriented relative thereto. Motor 110 rotates shaft 14 about the axis "B-B" relative to housing 20 of handle assembly 12 at a radial speed proportional to the rotation of rotation control 300 from the home position about the control axis, similarly as detailed above with respect to motion sensing assembly 100 (FIG. 1).

Similarly, rotation of the rotation control 300 in a counter-clockwise direction rotates shaft 14 about the axis "B-B" relative to housing 20 of handle assembly 12 in a counter-clockwise direction. Rotation control 300 may be a return-to-center potentiometer such that when rotation control 300 is released, rotation control 300 returns to a home or neutral position; shaft 14 is fixed about the axis "B-B" relative to housing 20 of handle assembly 12 when rotation control 300 is in the neutral position. Rotation lockout features such as those detailed above may likewise be used in conjunction with rotation control 300. Alternatively, rotation control 300 may be an encoder or a return-to-center encoder and function in a similar manner as detailed above with respect to the potentiometer and return-to-center potentiometer, respectively. In embodiments where rotation control 300 is an encoder or a return-to-center encoder, various methods of encoding input may be provided such as, for example, electrical pulses or optics.

Figure 4A:
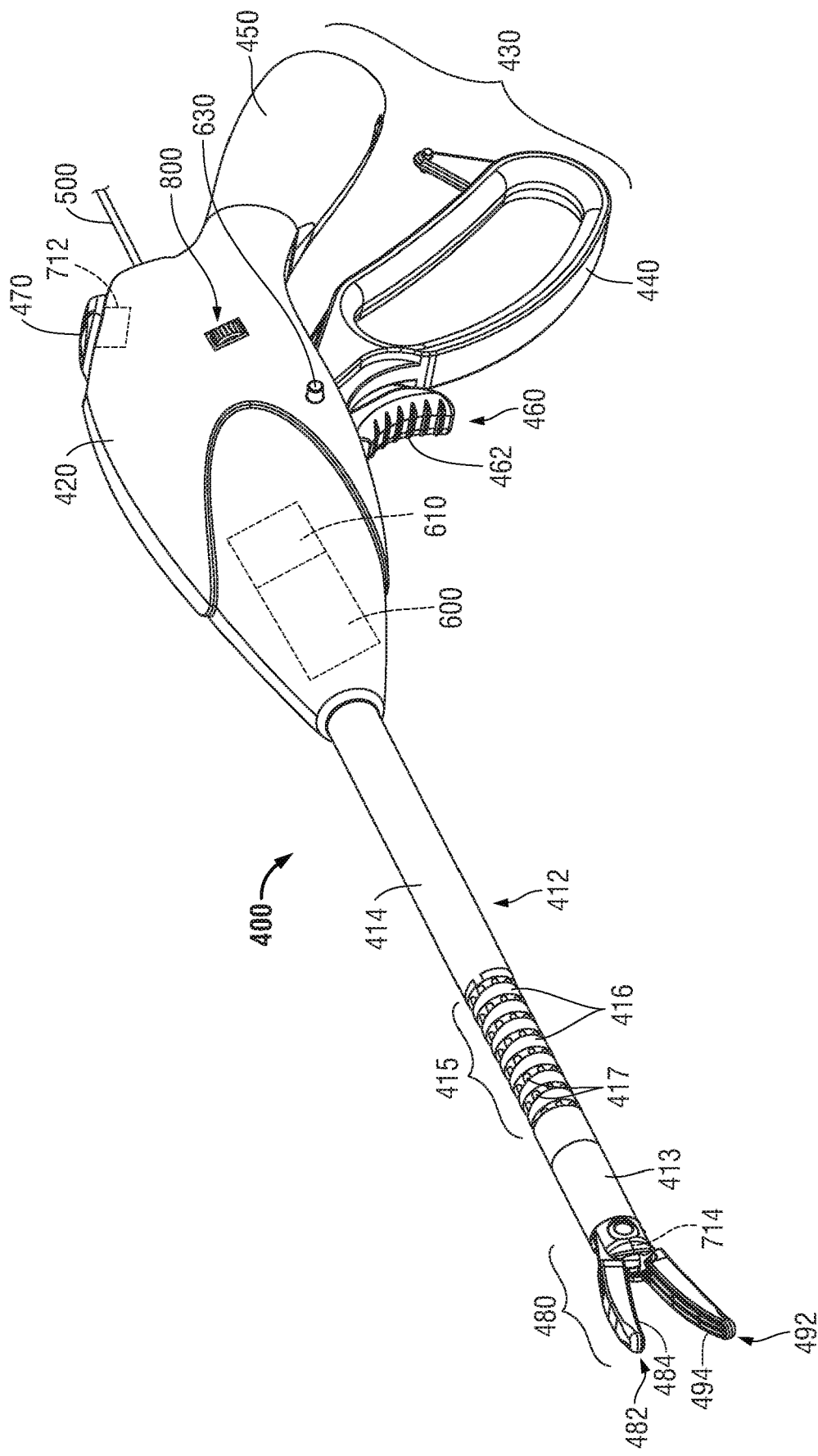
FIG. 4A is a perspective view of another surgical instrument provided in accordance with aspects of the present disclosure with jaw members of the end effector assembly thereof disposed in a spaced-apart position.
Figure 4B:
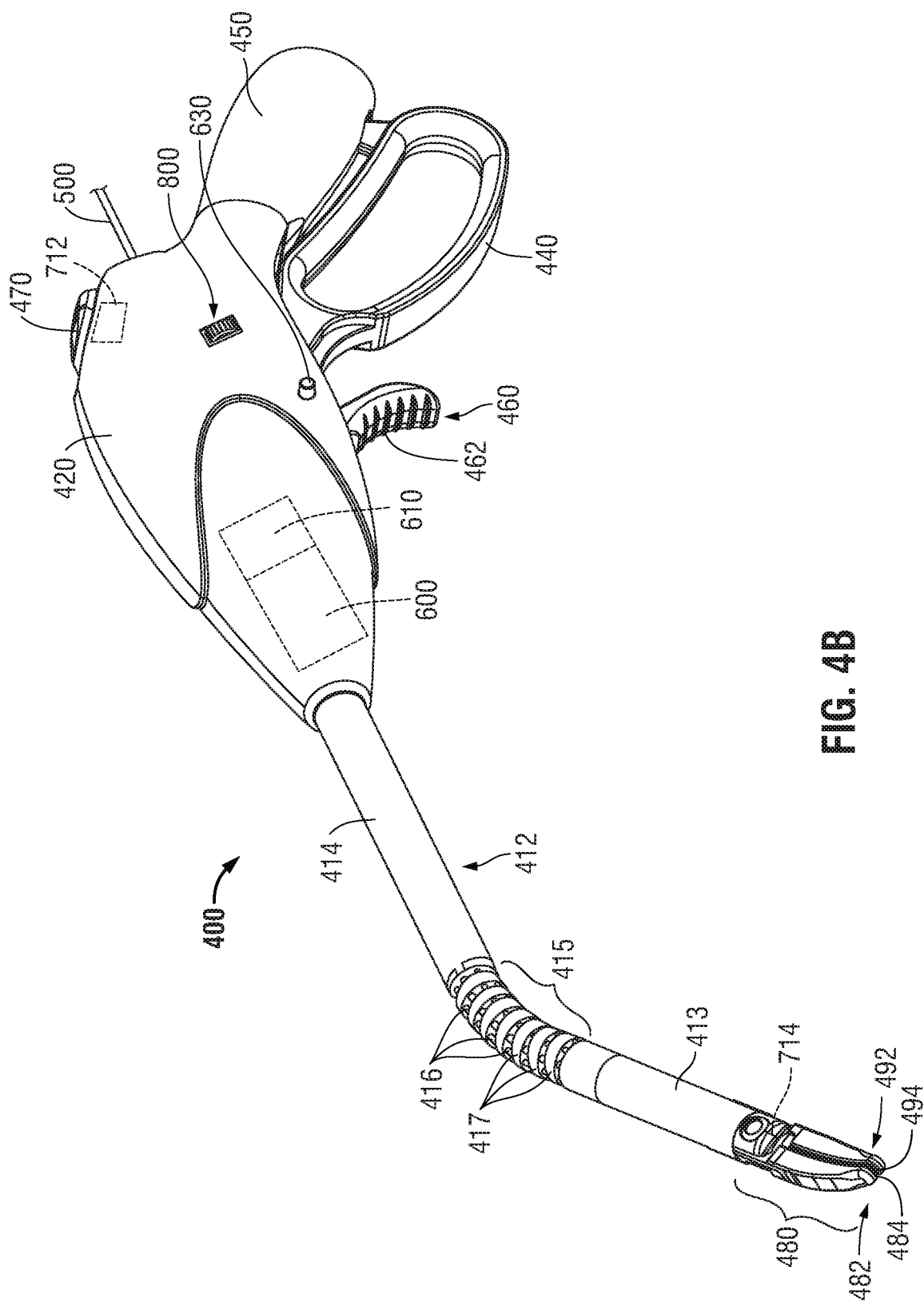
FIG. 4B is a perspective view of the surgical instrument of FIG. 4A, wherein the end effector assembly thereof is disposed in an articulated position and the jaw members disposed in a spaced-apart position.

Referring to FIGS. 4A and 4B, an endoscopic electrosurgical surgical instrument exemplifying aspects and features of the present disclosure is shown generally identified by reference numeral 400. Endoscopic electrosurgical surgical instrument 400 includes a housing 420, a handle assembly 430, a trigger assembly 460, an activation switch 470, and an end effector assembly 480. Instrument 400 further includes a shaft 412 having a distal end portion configured to mechanically engage end effector assembly 480 and a proximal end portion that mechanically engages housing 420. A cable 500 connects instrument 400 to an electrosurgical generator (not shown), although instrument 400 may alternatively be configured as a battery-powered device. Cable 500 includes wires (not shown) extending therethrough that have sufficient length to extend through shaft 412 in order to provide electrosurgical energy to one or both tissue-treating surfaces 484, 494 of jaw members 482, 492, respectively, of end effector assembly 480. Activation switch 470 is coupled to tissue-treating surfaces 484, 494 and the generator for selectively activating the supply of energy to jaw members 482, 492 for treating, e.g., cauterizing, coagulating/desiccating, and/or sealing, tissue.

Shaft 412 defines a distal segment 413 positioned towards the distal end portion thereof, a proximal segment 414 positioned towards the proximal end portion thereof, and an articulating section 415 disposed between the distal and proximal segments 413, 414, respectively. Articulating section 415 includes a plurality of articulating links 416 having a plurality of articulation cables 417 extending therethrough. Each cable 417 is operably engaged at its distal end to distal segment 413 or one of the articulating links 416 and at its proximal end to the articulation actuator, e.g., motion sensing assembly 600 and/or rotation/articulation control assembly 800, so as to enable articulation of distal segment 413 and, thus, end effector assembly 480, relative to proximal segment 414 upon actuation of the articulation actuator. In some embodiments, articulating section 415 is omitted, such that shaft 412 does not articulate.

Handle assembly 430 of instrument 400 includes a fixed handle 450 and a movable handle 440. Fixed handle 450 is integrally associated with housing 420 and movable handle 440 is movable relative to fixed handle 450. Movable handle 440 of handle assembly 430 is operably coupled to a drive assembly (not shown) that, together, mechanically cooperate to impart movement of one or both of jaw members 482, 492 of end effector assembly 480 between a spaced-apart position (FIG. 4A) and an approximated position (FIG. 4B) to grasp tissue between jaw members 482, 492, in response to actuation of movable handle 440.

Trigger assembly 460 includes a trigger 462 coupled to housing 420 and movable relative thereto between an un-actuated position and an actuated position. Trigger 462 is operably coupled to a knife (not shown) that is selectively translatable between jaw members 482, 492 in response to activation of trigger 462 to cut tissue grasped between jaw members 482, 492.

End effector assembly 480, as noted above, includes first and second jaw members 482, 492 pivotably coupled to one another to enable movement of one or both of jaw members 482, 492 between the spaced-apart and approximated positions. Tissue-treating surfaces 484, 494 of jaw members 482, 492, respectively, are positioned to oppose one another, grasp tissue therebetween, and are formed from an electrically conductive material to enable conduction of electrosurgical energy therebetween for treating tissue grasped therebetween. As mentioned above, tissue-treating surfaces 484, 494 are coupled to activation switch 470 and the generator (not shown) such that energy may be selectively supplied tissue-treating surfaces 484, 494 and conducted through tissue disposed therebetween to treat tissue in response to activation of activation switch 470.

Instrument 400 may further include a motion activation control 630 and motion sensing assembly 600 including a motor 610, similar to motion activation control 30, motion sensing assembly 100, and motor 110, respectively, of instrument 10 (see FIG. 1), to enable setting of a reference position and, thereafter, rotation of shaft 412 and, thus, end effector assembly 480 relative to housing 420 in response to movement of housing 420 relative to the reference position. As an alternative to or in addition to controlling rotation of shaft 412, motor 610 (or a separate motor (not shown)) may be operably coupled to articulation cables 417 to enable setting of a reference position of housing 420 for articulation (which may be similar or different from the reference position for rotation) and, thereafter, articulation of end effector assembly 480 relative to housing 420 in response to movement of housing 420 relative to the reference position for articulation. In embodiments, once an articulated position is achieved, this articulated position may be maintained when a rotational input is received to prevent the articulated end effector assembly 480 from whipping around as a result of rotation of shaft 412 and, instead, provide wristed rotation of end effector assembly 480 in the articulated position.

Rotation and/or articulation lockout features may be incorporated into instrument 400 to prevent rotation and/or articulation of end effector assembly 480 when certain conditions are met. For example, the rotation lockout feature can include a lockout switch 712 engagable by activation switch 470 such that when activation switch 470 is depressed to deliver electrosurgical energy, lockout switch 712 signals to the microcontroller of motion sensing assembly 600 to prevent rotation and/or articulation of end effector assembly 480. Additionally or alternatively, the rotation lockout feature may prevent rotation and/or articulation of end effector assembly 480 when jaw members 482, 484 are disposed in the approximated position via a lockout switch 714 disposed at end effector assembly 480 (or otherwise positioned) such that when jaw members 482, 484 are disposed in the approximated position, lockout switch 714 signals the microcontroller of motion sensing assembly 600 to prevent rotation and/or articulation of end effector assembly 480. Instrument 400 may also include a torque limiting mechanism 720, similarly as detailed above, that prevents excessive torque from being applied by motor 610 to rotate and/or articulate end effector assembly 480.

As an alternative to or in addition to incorporating motion sensing assembly 600, instrument 400 may include a rotation/articulation control assembly 800 to control rotation and/or articulation of end effector assembly 480. For example, in embodiments, one of motion sensing assembly 600 and rotation/articulation control assembly 800 controls rotation, while the other of motion sensing assembly 600 and rotation/articulation control assembly 800 controls articulation, although other configurations are also contemplated. Rotation/articulation control assembly 800 is similar to rotation control 300 of instrument 10 (see FIG. 3), detailed above, and may likewise include lockout features.

In embodiments where motion sensing assembly 600 is utilized to control both rotation and articulation of end effector assembly 480, a first type of motion may effect rotation and a second type of motion may effect articulation. For example, rotation of housing 420 about a longitudinal axis of instrument 400 may effect rotation of end effector assembly 480, while tilting housing 420, e.g., up, down, left, or right from a neutral (reference) position, may effect articulation of end effector assembly 480 in a corresponding direction. Motion sensing assembly 600 may incorporate lockout features (not shown) to inhibit rotation while articulation is being effected and/or to inhibit articulation while rotation is being effected.

Figure 5:
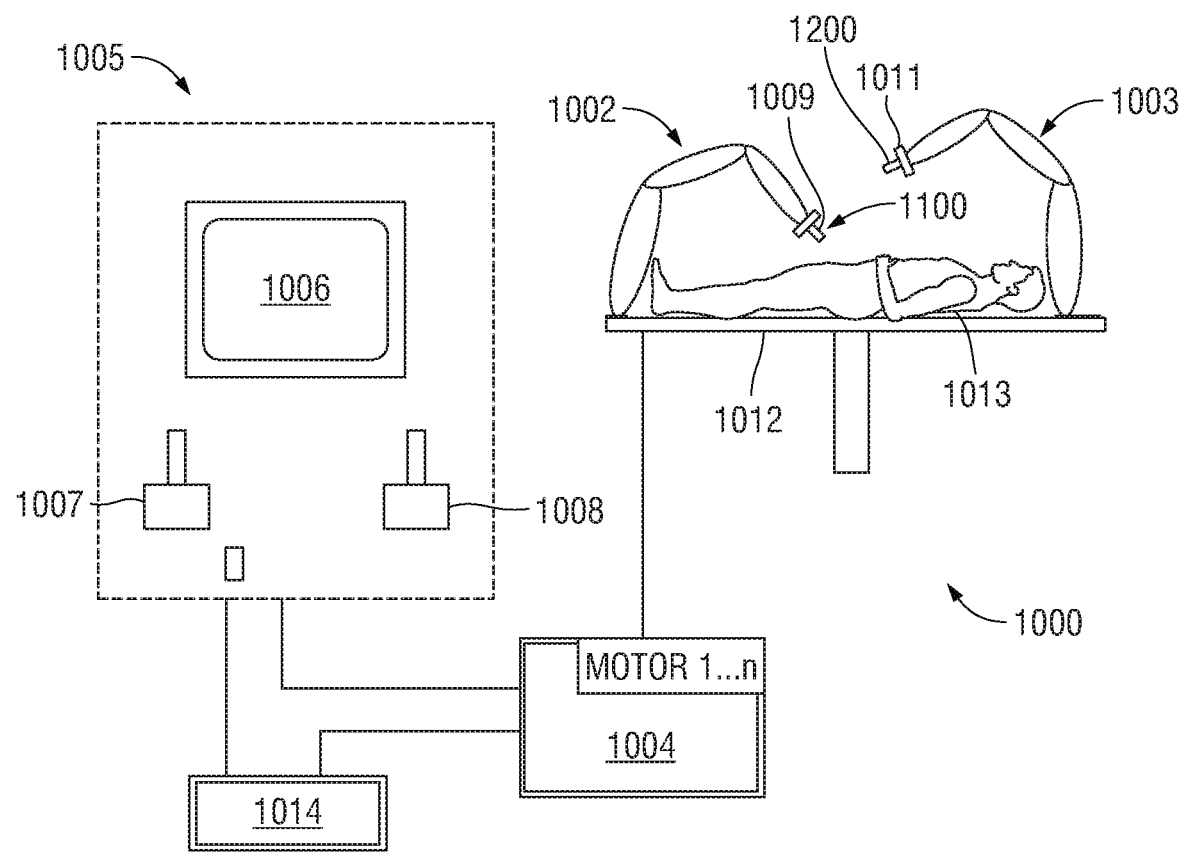
FIG. 5 is a schematic diagram of a robotic surgical system provided in accordance with aspects of the present disclosure.

With reference to FIG. 5, a robotic surgical system exemplifying the aspects and features of the present disclosure is shown identified by reference numeral 1000. Robotic surgical system 1000 includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, to enable a surgeon may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, an end effector assembly 1100, 1200, respectively. End effector assembly 1100 may be similar to end effector assemblies 100, 480 (FIGS. 1 and 4A, respectively), or any other suitable end effector assembly for coupling to attaching device 1009 may be provided. End effector assembly 1200 may be any end effector assembly, e.g., an endoscopic camera, other surgical tool, etc. Robot arms 1002, 1003 and end effector assemblies 1100, 1200 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and end effector assemblies 1100, 1200 execute a desired movement and/or function according to a corresponding input from manual input devices 1007, 1008, respectively. Control device 1004 may also be configured in such a way that it regulates the movement of robot arms 1002, 1003 and/or of the motors.

Manual input devices 1007, 1008 of robotic surgical system 1000 may further include a motion activation control, a motion sensing assembly including a motor, rotation and/or articulation lockout features, excessive torque limiting features, and/or a rotation control, similarly as detailed above, to provide the user with the ability to control manipulation of end effector assemblies 1100, 1200, similarly as detailed above with respect to instruments 10, 400 (FIGS. 1 and 4A, respectively) by moving manual input devices 1007, 1008 relative to a reference position.

Turning to FIG. 6, a surgical system 1600 provided in accordance with the present disclosure is illustrated including instrument 400 (although instrument 10 (FIG. 1), robotic surgical system 1000 (FIG. 5), or any other suitable surgical instrument or system may similarly be utilized), a surgical camera 1610, e.g., an endoscopic camera, and one or more surgical displays 1620, wherein end effector assembly 480 of instrument 400 and distal portion 612 of surgical camera 610 extend endoscopically into an internal surgical site "S."

Instrument 400 may include any or all of the features detailed above with respect to instrument 400 (or instrument 10 (FIG. 1) or robotic surgical system 1000 (FIG. 5)). In embodiments, instrument 400 may further include a position sensor 490 disposed on or within shaft 412 or end effector assembly 480. Position sensor 490 communicates with motion sensing assembly 600 and/or rotation/articulation control assembly 800 of instrument 400 to provide position information of end effector assembly 480 thereto. Alternatively, position sensor 490 may communicate the position information of end effector assembly 480 to display 1620 via a wireless or wired connection 1630 and/or to surgical camera 1610 via a wireless or wired connection 1640.

The position of end effector assembly 480 relative to the position of distal working end 1612 of surgical camera 1610 enables determination of whether motion sensing assembly 600 and/or rotation/articulation control assembly 800 should operate in a standard mode or in a reversed mode, as detailed below. As an alternative or in addition to providing a position sensor 490, instrument 400 may include a manual selector 492 enabling a user to manually select between the standard mode (a first position 492 of manual selector 492) or the reversed mode (a second position 494 of manual selector 492). Where both position sensor 490 and manual selector 492 are provided, manual selector 492 may include a neutral position 495, wherein the mode is automatically selected using position information, and may be movable from neutral position 495 to first position 493, wherein the standard mode is utilized regardless of the position information, or second position 494, wherein the reversed mode is utilized regardless of the position information.

In the standard mode, motion sensing assembly 600 and/or rotation/articulation control assembly 800 operate as detailed above; that is, where movement of housing 420 effects rotation and/or articulation of end effector assembly 480 in a corresponding direction, e.g., clockwise rotation of housing 420 effects clockwise rotation of end effector assembly 480. In the reversed mode, on the other hand, motion sensing assembly 600 and/or rotation/articulation control assembly 800 operate in a reversed manner; that is, where movement of housing 420 effects rotation and/or articulation of end effector assembly 480 in an opposite direction, e.g., clockwise rotation of housing 420 effects counterclockwise rotation of end effector assembly 480.

Continuing with reference to FIG. 6, surgical camera 1610 may be any suitable surgical camera such as, for example, an endoscopic camera including a distal working portion 1612 configured to be inserted into internal surgical site "S," an image capture portion 1614 disposed on distal working portion 1612, and a proximal handle assembly 1616. Image capture portion 1614 may include, for example, a lens and an image sensor, although other suitable components facilitating image capture are also contemplated. Surgical camera 1610 further includes, for example, an image processor 1618 and a transmitter 1619, e.g., a wireless or wired transmitter, associated with proximal handle assembly 1616 or otherwise incorporated into surgical camera 1610. As such, surgical camera 1610 is configured to convert an optical image produced by the lens into an electrical signal for transmission to surgical display 1620 via a wireless or wired connection 1650. Surgical camera 1610 may further include an illumination source (not shown) to facilitate visualization within the internal surgical site "S." Additionally or alternatively, surgical camera 1610 may include a position sensor 1613 disposed at distal working portion 1612 thereof that is configured to communicate position information of distal working portion 1612 to instrument 400 via wireless or wired connection 1640, or to surgical display 1620 via wireless or wired connection 1650.

Surgical display 1620 includes a display monitor 1622 and a CPU 1624 including, for example, a processor and memory associated therewith storing instructions for execution by the processor. Surgical display 1620 further includes a transmitter 1626, e.g., a wireless or wired transmitter, configured to receive the electrical signals from surgical camera 1610 via wireless or wired connection 1650 and, in embodiments, the position information from position sensor 1613 of surgical camera 1610 and/or the position information from position sensor 490 of instrument 400 via wireless or wired connections 1630, 1650, respectively.

Continuing with reference to FIG. 6, in use, surgical display 1620 is configured to receive the electrical signals from surgical camera 1610 and display a corresponding video image of the internal surgical site "S" on display monitor 1622 to enable the surgeon to view the internal surgical site "S" on display monitor 1622 and, more specifically, to enable the surgeon to view end effector assembly 480 on display monitor 1622, thus facilitating manipulation of end effector assembly 480 into position for performing a surgical task, e.g., grasping, treating, and/or dividing tissue.

Depending upon the position of end effector assembly 480 relative to surgical camera 1610, the video image displayed on display monitor 1622 may become reversed. In such an instance, when the surgeon manipulates, e.g., translates, rotates, and/or articulates, end effector assembly 480 in one direction, the video image displayed on display monitor 1622 displays the manipulation of end effector assembly 480 in an opposite direction. Such is sometimes referred to as reverse alignment visualization.

In embodiments, motion sensing assembly 600 and/or rotation/articulation control assembly 800 may determine, based upon the position information received from position sensors 490, 1613, whether the relative positions of end effector assembly 480 and surgical camera 1610 would result in reverse alignment visualization of the video image displayed on display monitor 1622. If it is determined that reverse alignment visualization would result, motion sensing assembly 600 and/or rotation/articulation control assembly 800 is automatically switched to the reversed mode such that the surgeon, when viewing display monitor 1622, can move housing 420 of instrument 400 in a desired direction to effect corresponding rotation and/or articulation of end effector assembly 480 as it appears on display monitor 1622 in the same direction (which is opposite the direction of rotation and/or articulation of end effector assembly 480 within the internal surgical site "S").

If it is determined that reverse alignment visualization would not result, motion sensing assembly 600 and/or rotation/articulation control assembly 800 is automatically switched to the standard mode such that the surgeon, when viewing display monitor 1622, can move housing 420 of instrument 400 in a desired direction to effect corresponding rotation and/or articulation of end effector assembly 480 as it appears on display monitor 1622 in the same direction (which is the same direction of rotation and/or articulation of end effector assembly 480 within the internal surgical site "S").

As an alternative to motion sensing assembly 600 and/or rotation/articulation control assembly 800 determining whether reverse alignment visualization would result, the position information may be communicated to display 1620 or surgical camera 1610 to enable display 1620 or surgical camera 1610 to determine whether reverse alignment visualization would result in a similar manner as detailed above. The display 1620 or surgical camera 1610 may then relay the result back to motion sensing assembly 600 and/or rotation/articulation control assembly 800 to automatically adjust the mode (in embodiments where the mode is automatically adjusted or in manual embodiments where manual selector 392 is disposed in neutral position 495), if necessary, or may provide an indicator (audible, tactile, or visual indicator) to enable the user to manually switch the mode, if desired, in embodiments where manual selector 492 is provided.

Additional or alternative hardware and/or software components, incorporated into instrument 400, surgical camera 1610, and/or display 1620, may be provided to enable determination of whether reverse alignment visualization would result. Further, whether reverse alignment visualization would result may be determined periodically at any suitable interval, dynamically, e.g., upon movement of end effector assembly 480 or surgical camera 1620, or in any other suitable manner. In embodiments where lockout features, torque limiting features, or other safety features, the activation of the same may be communicated to display 1620 for display or other output of a suitable indicator to indicate to the surgeon that the lockout feature, torque limiting feature, or other safety feature has been activated. Likewise, display 1620 (and/or instrument 400) may display or otherwise indicate whether motion sensing assembly 600 and/or rotation/articulation control assembly 800 is operating in the standard mode or the reversed mode via a suitable indicator.

In embodiments where multiple displays 1620 are provided, the displays 1620 may be configured to operate in the same mode, in opposite modes, or independently based upon different feedback or other input.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A surgical instrument, comprising:
    a housing;
    a shaft extending distally from the housing;
    an end effector assembly extending distally from the shaft, wherein the end effector assembly is configured to at least one of rotate or articulate relative to the housing;
    a motor disposed within the housing and operably coupled to the end effector assembly to at least one of rotate or articulate the end effector assembly relative to the housing; and
    a sensing assembly configured to sense movement of the housing relative to a reference position and to drive the motor to at least one of rotate or articulate the end effector assembly relative to the housing based upon the sensed movement,
    wherein the sensing assembly is configured to operate in each of a standard mode, wherein a movement of the housing relative to the reference position effects at least one of rotation or articulation of the end effector assembly in a first direction, and a reversed mode, wherein the movement of the housing relative to the reference position effects at least one of rotation or articulation of the end effector assembly in a second direction opposite the first direction.

2. The surgical instrument according to claim 1, wherein the end effector assembly is at least one of rotated or articulated at a speed proportional to displacement of the housing from the reference position.

3. The surgical instrument according to claim 2, wherein the end effector assembly is at least one of rotated or articulated at a speed proportional to displacement of the housing from the reference position up to a maximum speed.

4. The surgical instrument according to claim 1, wherein the motor is configured to rotate and articulate the end effector assembly.

5. The surgical instrument assembly according to claim 1, further comprising a second motor disposed in the housing and operably coupled to the end effector assembly, wherein the first motor is configured to one of rotate or articulate the end effector assembly and the second motor is configured to the other of rotate or articulate the end effector assembly.

6. The surgical instrument according to claim 1, further comprising a rotation lockout configured to prevent rotation of the end effector assembly in response to a sensed condition.

7. The surgical instrument according to claim 1, further comprising a manual selector associated with the housing and selectively movable to a first position or a second position to switch to the standard mode or the reversed mode, respectively.

8. The surgical instrument according to claim 7, wherein the manual selector further includes a neutral position wherein the sensing assembly automatically switches between the standard mode and the reversed mode.

9. The surgical instrument according to claim 1, wherein the sensing assembly automatically switches between the standard mode and the reversed mode based upon a position of the end effector assembly.

10. The surgical instrument according to claim 9, wherein the sensing assembly automatically switches between the standard mode and the reversed mode based upon a position of the end effector assembly relative to a surgical camera.

11. A surgical system, comprising:
a surgical camera;
a surgical display configured to display a video image received from the surgical camera;
a housing and an end effector assembly distally-spaced from the housing, the end effector assembly configured to at least one of rotate or articulate relative to the housing; and
a sensing assembly configured to sense an input movement relative to a reference position and to effect at least one of rotation or articulation of the end effector assembly relative to the housing in response to the sensed input movement relative to the reference position,
wherein the sensing assembly is configured to operate in each of a standard mode, wherein the sensed input movement relative to the reference position effects at least one of rotation or articulation of the end effector assembly in a first direction, and a reversed mode, wherein the sensed input movement relative to the reference position effects at least one of rotation or articulation of the end effector assembly in a second direction opposite the first direction.

12. The surgical system according to claim 11, wherein the sensing assembly operates in the standard mode when reverse alignment visualization of the video image does not occur, and wherein the sensing assembly operates in the reversed mode when reverse alignment visualizing of the video image occurs.

13. The surgical system according to claim 12, wherein the sensing assembly automatically switches between the standard mode and the reversed mode based upon whether reverse alignment visualization occurs.

14. The surgical system according to claim 12, wherein an indicator is provided to indicate to a user to switch to the standard mode or the reversed mode based upon whether reverse alignment visualization occurs.

15. The surgical system according to claim 12, further comprising at least one position sensor operably associated with at least one of the end effector assembly or the surgical camera and configured to detect a position thereof, and wherein the occurrence of reverse alignment visualization is determined based upon the position of the end effector assembly or the surgical camera.

16. The surgical system according to claim 15, wherein a first position sensor of the at least one position sensor is operably associated with the end effector assembly and a second position sensor of the at least one position sensor is associated with the surgical camera, and wherein the occurrence of reverse alignment visualization is determined based upon the relative positions of the end effector assembly and the surgical camera.

17. The surgical system according to claim 11, further including a manual selector associated with the housing and selectively movable to a first position or a second position to switch to the standard mode or the reversed mode, respectively.

18. The surgical system according to claim 17, wherein the manual selector further includes a neutral position wherein the sensing assembly automatically switches between the standard mode and the reversed mode based upon whether reverse alignment visualization occurs.

19. The surgical system according to claim 17, wherein an indicator is provided to indicate occurrence of reverse alignment visualization to indicate to a user to move the manual selector to the second position.

20. The surgical system according to claim 11, further including a rotation lockout configured to prevent rotation of the end effector assembly in response to a sensed condition.

* * * * *